US006955921B2

(12) United States Patent
Corey et al.

(10) Patent No.: US 6,955,921 B2
(45) Date of Patent: Oct. 18, 2005

(54) TRYPSIN SUBSTRATE AND DIAGNOSTIC DEVICE, AND METHOD OF USING SAME

(75) Inventors: Paul F. Corey, Elkhart, IN (US); Steven W. Felman, Granger, IN (US); Gary E. Rehm, Tucson, AZ (US); Michael J. Pugia, Granger, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 10/287,239

(22) Filed: Nov. 4, 2002

(65) Prior Publication Data

US 2003/0125577 A1 Jul. 3, 2003

Related U.S. Application Data

(62) Division of application No. 09/844,816, filed on Apr. 30, 2001, now Pat. No. 6,770,764.

(51) Int. Cl.$^7$ ........................ G01N 21/64; G01N 33/68; G01N 33/573; G01N 33/48
(52) U.S. Cl. ........................ 436/172; 436/87; 435/23
(58) Field of Search ............................. 435/23; 436/87, 436/172

(56) References Cited

U.S. PATENT DOCUMENTS

| | | | |
|---|---|---|---|
| 3,552,928 A | 1/1971 | Fetter ........................... | 23/253 |
| 3,846,247 A | 11/1974 | Kronish et al. ............. | 195/127 |
| 3,897,214 A | 7/1975 | Lange et al. .................. | 23/253 |
| 4,046,513 A | 9/1977 | Johnston ...................... | 23/253 |
| 4,046,514 A | 9/1977 | Johston et al. ................ | 23/253 |
| 4,551,428 A | 11/1985 | Berger et al. ................. | 435/19 |
| 4,645,842 A | 2/1987 | Corey ......................... | 548/541 |
| 4,657,855 A | 4/1987 | Corey et al. .................. | 435/19 |
| 4,704,460 A | 11/1987 | Corey ......................... | 549/65 |
| 4,717,658 A | 1/1988 | Michaels ..................... | 435/19 |
| 4,774,340 A | 9/1988 | Corey et al. ................. | 548/541 |
| 5,750,405 A | 5/1998 | Albarella et al. ............. | 436/88 |
| 6,583,108 B1 | 6/2003 | Tamburini et al. | |

FOREIGN PATENT DOCUMENTS

| | | |
|---|---|---|
| GB | 1349623 | 4/1974 |
| GB | 1369139 | 10/1974 |
| JP | 11-75896 | 3/1999 |

OTHER PUBLICATIONS

Aogaichi T & Plaut GWE, "Assay of the esterase activity of thrombin, plasmin and trypsin with a chromogenic substrate p–nitrobenzyl p–toluenesulfonyl–l–arginine", *Thrombos. Haemostas.* (*Stutg.*) 37: 253–261 (1977).
Baustert JH et al., "Fluorometric continuous kinetic assay of α–chymotrypsin using new protease substrates possessing long–wave excitation and emission maxima", *Analytical Biochemistry* 171: 393–397 (1988).
Chem Sources–U.S.A. (Chemical Sources International, Inc., 1999) [Title Page].

Desnuelle P, "Trypsin", *The Enzymes, Second Edition*, Chapter 6, pp.—119–132 (Academic Press, New York and London, 1960).
Goldbarg JA & Rutenburg AM., "The colorimetric determination of leucine aminopeptidase in urine and serum of normal subjects and patients with cancer and other diseases." *Cancer* 11: 283 (1958).
Gray CJ et al., 4–methylumbelliferyl esters as fluorogenic substrates for proteases. *Enzyme Microb. Technol.* 5: 137 (1983).
Higashi S et al., "Tissue Factor Potentiates the Factor VIIa–catalyzed Hydrolysis of an Ester Substrate", *J. Biol. Chem.* 267(25): 17990–17996 (Sep. 5, 1992).
Inouye K et al., "Synthesis of TACK, a new chloromethyl ketone derivative of arginine.", *Bull. Chem Soc. Japan* 47(1): 202 (1974).
Jensen KA & Crossland I, "Studies of thioacids and their derivatives. VII. On 2–phenyl–4(5H)–thiazolone." *Acta Chem. Scand*: 17: 144 (1963).
Kuwajima S et al., "Automated measurement of trypsin inhibitor in urine with a centrifugal analyzer: comparison with other acute phase reactants." *Clin. Biochem.* 23: 167 (1990).
Leytus SP et al., "Rhodamine–based compoundsa s fluorogenic substrates for serine proteinases", *Biochem, J.* 209: 299–307 (1983).
Piette AM et al., "Urinary trypsin inhibitory activity for the diagnosis of bacterial infection: a prospective study in 690 patients." *European J. Med.* 1: 273 (1992).
*Technical Data on Methods of Measuring Urinary Trypsin Inhibitor (UTI)* (Sakamoto, Kyoto Daiichi Kagaku Co., Ltd., Feb. 25, 1997).

*Primary Examiner*—Mary E. Ceperley
(74) *Attorney, Agent, or Firm*—McDermott Will & Emery LLP

(57) ABSTRACT

A compound of the formula (I)

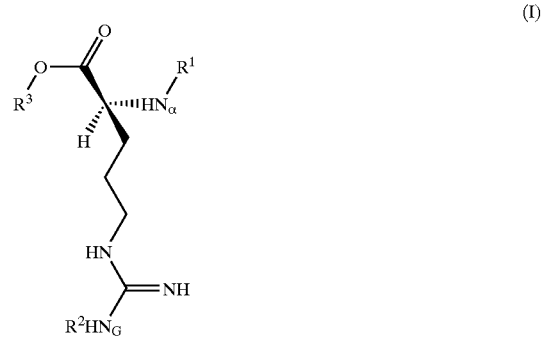

wherein $R^1$ is a protecting group for $N\alpha$, $R^2$ is a protecting group for $N_G$, and $R^3$ is aryl, and wherein the compound of formula (I) is a trypsin substrate such that trypsin cleaves the O—C single bond, which liberates $R^3$—OH; a diagnostic device comprising same; a method for preparing the diagnostic device; and a method of using the diagnostic device to detect levels of urinary trypsin inhibitor in a biological sample; and a diagnostic kit for detecting levels of urinary trypsin inhibitor in a biological sample.

17 Claims, No Drawings

TRYPSIN SUBSTRATE AND DIAGNOSTIC DEVICE, AND METHOD OF USING SAME

This is a request for filing a divisional application under 37 C.F.R. § 1.53(b) of U.S. patent application Ser. No. 09/844,816, filed on Apr. 30, 2001, now U.S. Pat. No. 6,770,764 entitled: TRYPSIN SUBSTRATE AND DIAGNOSTIC DEVICE, AND METHOD OF USING SAME.

BACKGROUND OF THE INVENTION

Urinary trypsin inhibitor ("UTI") is a glycoprotein that inhibits the enzyme reactivity of trypsin and α-chymotrypsin, hyaluronidase, and creatine phosphokinase. UTI can be present in minute quantities in the urine of healthy individuals.

Trypsin inhibitor activity has been suggested for use in a screening test for diagnosing bacterial infection. When bacterial infections occur, white blood cells are mobilized, and the elastase activity of the white blood cells is activated. During the acute phase response, interleukin-1 induces the production of inter-α-trypsin inhibitor, which is decomposed by the elastase activity into low molecular weight trypsin inhibitors. These trypsin inhibitors appear to act on the inflamed sites, showing anti-inflammatory and anti-shock activities before being excreted in the urine. Piette et al. (*European J. Med.* 1, 273 (1992)) reports that urinary trypsin inhibitor activity can be a useful marker, particularly in patients with fever of unknown origin or elevated erythrocyte sedimentation rate.

Quantitative changes in UTI are useful as an index of infection or inflammation. Kuwajima et al. (*Clin. Biochem.* 23, 167 (1990)) reports that the assay of UTI may be used for the clinical diagnosis of acute phase response. UTI levels are elevated under other circumstances such as malignant tumors, kidney disease, myocardial infarction and post surgery.

Serum C-reactive protein, sialic acid and erythrocyte sedimentation rate have been used as markers of infection and inflammation. However, all of these markers are serum-based, which requires a blood sample. Using blood samples requires time for coagulation, centrifugation, and separation of the blood sample before analysis.

Measuring UTI concentration has been accomplished several ways, including enzyme inhibition, antibody stains, latex agglutination methods and radioimmunoassay methods. Enzyme inhibition has been used to measure UTI concentration, and colorimetric enzyme substrates have been used to measure the extent of the inhibition. The method has been recently adapted to automated measurement on clinical analyzers (S. Kuwajima, et al., loc. cit.). Such analytical techniques typically involve contacting the urine sample with a trypsin substrate attached to a chromophore at either arginine or lysine, because trypsin cleaves arginine and lysine. The concentration of UTI in the urine sample is inversely proportional to the intensity of the colored response of the chromophore since UTI inhibit trypsin activity according to their concentration in the fluid test sample.

Several colorimetric and fluorogenic trypsin substrates are commercially available, including Nα-benzoyl-L-arginine p-nitroanilide (BAPNA), Nα-benzoyl-D,L-arginine β-naphthylamide (BANA) and Nα-benzoyl-L-arginine-7-amido-4-methylcournarin.

Known indicating trypsin substrates are aromatic amides of Nα-protected arginine. When trypsin hydrolyzes these known substrates, the amide bond is cleaved and an aromatic amine is released. In the case of BAPNA, the amide bond is cleaved and yellow-colored p-nitroaniline is liberated and measured with a spectrophotometer. With BANA, 2-aminonaphthalene is produced, and it is detected by diazotization and coupling with N-(1-naphthyl)-ethylenediamine to form an azo dye (Goldberg, et al., *Cancer* 11, 283 (1958)). 7-Amino-4-methylcoumarin is released by hydrolysis of Nα-benzoyl-L-arginine-7-amido-4-methylcoumarin, and this fluorescent product is measured with a fluorometer. These substrates are used for measuring trypsin activity in liquid-phase assays but are not well suited for use in dry-phase formats, such as dip-sticks, which are typically read visually or with simple reflectance instruments.

Aromatic esters of arginine are not known to those of skill in the art as trypsin substrates. Esters are much more labile toward hydrolysis than amides, and are often incorporated into protease substrates in place of amides to give more sensitive, easily hydrolysed analogs. They are also more prone to non-enzymatic hydrolysis by nucleophiles. This is significant for arginine esters, which have the nucleophilic guanidino group as part of their structure. Gray, et al. (*Enzyme Microb. Technol.* 5, 137 (1983)) states that efforts to prepare the Nα-benzoyl-arginine esters of 2-hydroxynaphthol and 7-hydroxy-4-methylcoumarin were unsuccessful because of the lability of the ester group.

A trypsin substrate is needed that addresses the shortcomings of prior art including, among other things, the requirement of a blood sample.

SUMMARY OF THE INVENTION

This invention provides aromatic esters of Nα-(α amino group) and $N_G$-(guanidino group) bis-protected arginine that are trypsin substrates. Surprisingly, trypsin hydrolyzes esters of arginine with protecting groups on the guanidino moiety. The esters of the present invention may be used to produce visible colors in dry-phase analytical elements to detect quantities of UTI in biological sample such as urine.

In one aspect of the invention, a compound of the formula (I) comprises:

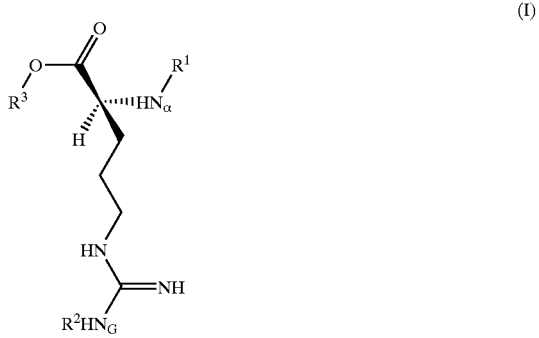

wherein $R^1$ is a protecting group for Nα, $R^2$ is a protecting group for $N_G$; and $R^3$ is aryl; and wherein the compound of formula (I) is a trypsin substrate such that trypsin cleaves the O—C single bond, which liberates $R^3$—OH.

In another aspect of the invention, a diagnostic device comprises a carrier matrix and a compound of the formula (I).

In another aspect of the invention, a method of preparing a diagnostic device comprises (a) contacting a carrier matrix with a buffer solution, (b) drying the carrier matrix, and (c) contacting the carrier matrix with a solution comprising the trypsin substrate of formula (I).

In still another aspect of the invention, a method for detecting levels of urinary trypsin inhibitor in a biological sample comprises (a) contacting a biological sample with a predetermined amount of trypsin, a predetermined amount of a diazonium salt, and a diagnostic device comprising a trypsin substrate of the formula (I) wherein $R^1$ is a protecting group for Nα; $R^2$ is a protecting group for $N_G$; and $R^3$ is aryl; and wherein the compound of formula (I) is a trypsin substrate such that trypsin cleaves the O—C single bond, which liberates $R^3$—OH; and wherein the compound $R^3$—OH reacts with a diazonium salt to form a visible color such that the greater the intensity of the color, the less urinary trypsin inhibitor is in the biological sample.

In still another aspect of the invention, a diagnostic kit for determining the presence of urinary trypsin inhibitor in a biological fluid comprises trypsin and a trypsin substrate of the formula (I).

The present invention provides the foregoing and other features, and the advantages of the invention will become further apparent from the following detailed description of the presently preferred embodiments. The detailed description is merely illustrative of the invention and does not limit the scope of the invention, which is defined by the appended claims and equivalents thereof.

DETAILED DESCRIPTION OF THE PREFERRED EMBODIMENTS

Definition of Terms

"Alkyl" as used herein is the radical of saturated aliphatic groups, including straight-chain alkyl groups, branched-chain alkyl groups and cycloalkyl groups. Particularly preferred alkyl substituents include methyl, ethyl, propyl, isopropyl, cyclopropyl, butyl, iso-butyl, tert-butyl, sec-butyl, pentyl, hexyl, cyclohexyl, etc. Unless the number of carbons is otherwise specified, "lower alkyl" as used herein means an alkyl group, as defined above, but having from one to ten carbons, more preferably from one to six carbon atoms in its backbone structure. The aliphatic cyclic groups can be single or polycyclic containing between about 1 to 12 carbons per ring, but preferably between 1 and 9 carbons per ring.

"Aryl" as used herein includes 5–15 membered aromatic monocyclic or fused polycyclic moieties which may include from zero to four heteroatoms selected from the group consisting of oxygen, sulfur and nitrogen. For example, benzene, pyrrole, furan, thiophene, imidazole, oxazole, thiazole, triazole, pyrazole, pyridine, pyrazine, pyridazine, pyrimidine, naphthylene, benzothiazole, benzothiaphene, benzofuran, indole, quinoline, etc. The aryl group can be substituted at one or more positions with halo, alkyl, hydroxy, alkoxy, alkoxy carbonyl, haloalkyl, cyano, amino sulfonyl, aryl, sulfonyl, aminocarbonyl, carboxy, acylamino, alkyl sulfonyl, amino and substituted or unsubstituted substituents, provided the substituent does not interfere with the ability of the composition of formula (I) to hydrolyze in the presence of trypsin.

"Heteroaryl" as used herein is a mono-, bi- or tricyclic, —N—, —O— or —S— heteroaryl substituent, such as benzofuran, benzothiophene, furan, imidazole, indole, isothiazole, oxazole, piperazine, pyrazine, pyrazole, pyridazine, pyridine, pyrimidine, pyrrole, quinoline, thiazole and thiophene.

"Protecting group" as used herein is a group that is used to protect a functional group from unwanted reactions. After application, the protecting group can be removed.

The Trypsin Substrate

The trypsin substrates of the present invention include aromatic esters of Nα,$N_G$-bis-protected-arginine and Nα,$N_G$-bis-protected-arginine derivatives. When the esters are hydrolyzed by trypsin, an aromatic alcohol is liberated, producing a readily detectable signal if trypsin is present in the biological sample.

The arginine esters are described generically as compounds of formula (I):

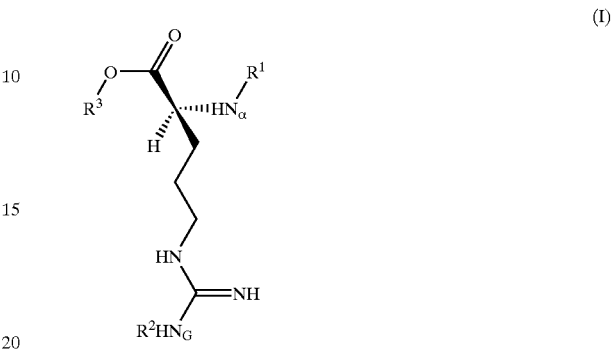

(I)

wherein $R^1$ is a protecting group for Nα; $R^2$ is a protecting group for $N_G$; and $R^3$ is aryl; and wherein the compound of formula (I) is a trypsin substrate such that trypsin cleaves the O—C single bond; which liberates $R^3$—OH. In one embodiment, $R^3$—OH is optically distinguishable from the compound of formula (I). In this embodiment, $R^3$—OH is preferably visually distinct (using only the naked eye) from the compound of formula (I). Alternatively, $R^3$—OH can be optically distinguishable from the compound of formula (I) using analytical instrumentation.

In another embodiment, $R^3$—OH reacts with a diazonium salt to form a visible color.

Esters of p-nitrophenol, which produce a yellow color upon hydrolysis, are useful for trypsin detection in samples with little or no intrinsic color. In colorful biological samples, such as urine or blood serum, however, interference from endogenous colored constituents is minimized by using a substrate that produces an intense absorption in the visible region of the spectrum, preferably >500 nm. For this reason, the preferred substrates are derivatives of aromatic alcohols that readily form intensely-colored azo dyes when coupled with aromatic diazonium salts.

These arginine esters are preferably prepared by esterification of the carboxyl moiety of an Nα,$N_G$-protected-arginine with an aromatic alcohol. Preferably, the ester and alcohol possess different optical properties or chemical reactivities. For example, esters of p-nitrophenol are colorless, but the free phenol is yellow at pH>7. Esters of 7-hydroxy-4-methylcoumarin are non-fluorescent, while the free hydroxy-coumarin is highly fluorescent. Esters of 3-hydroxy-5-phenylpyrrole are unreactive toward aromatic diazonium salts like 2-methoxy-4-morpholinobenzenediazonium chloride (MMBD), whereas 3-hydroxy-5-phenylpyrrole quickly reacts with MMBD to produce a brightly-colored azo dye.

Any of these optical or chemical differences may be used to detect UIT in a biological sample.

Protecting Groups for Nα

$R^1$ is a protecting group for Nα. Preferred Nα protecting groups are stable and render the Nα function inert under the conditions employed in the reactions involved in making the trypsin substrate and in the reactions involved where trypsin cleaves the O—C single bond of the ester functional group. The species of the Nα protecting group used is not critical so long as the derivatized amino group is stable to the conditions of the subsequent reactions and does not interfere with the ability of the composition to hydrolyze in the presence of trypsin.

Suitable protecting groups for $N\alpha$ include, but are not limited to, carbamates, amides and aryl sulfonamides. Carbamates include the $\tau$-butoxycarbonyl ($\tau$-BOC) group, the carbobenzyloxy (CBZ) group and others known in the art. Amide protecting groups include lower alkyl amides such as the acetyl group and aryl amides such as the benzoyl group. Suitable aryl sulfonamide groups include the benzene sulfonyl group, the $\rho$-toluenesulfonyl (tosyl) group and others known in the art. These and other suitable protecting groups may include those listed in the chapter entitled "Protection for the Amino Group" of the third edition (April 1999) of "Protecting Groups in Organic Synthesis" by Green and Wuts, which is hereby incorporated by reference.

Protecting Groups for $N_G$ $R^2$ is a protecting group for $N_G$, also known as the guanidine N of arginine. The presence of a protecting group on the $N_G$ reduces the nucleophilicity of the guanidine moiety. The protecting group protects the ester from non-enzymatic hydrolysis. Further, the $N_G$-protecting group does not completely inhibit enzymatic hydrolysis, so that these arginine esters are stable and useful as trypsin substrates.

Preferred $N_G$ protecting groups are stable and render the $N_G$ function inert under the conditions employed in the reactions involved in making the trypsin substrate and in the reactions involved where trypsin cleaves the O—C single bond of the ester functional group.

Suitable protecting groups for $N_G$ include, but are not limited to, nitro, arene sulfonyl compounds, and carbonyl derivatives. A non-limiting list of suitable $N_G$ protecting groups may include nitro, tosyl, p-methoxybenzenesulfonyl, carbonbenzyloxy, benzoyl, and similarly-structured protecting groups.

The Aryl Moiety that Forms the Aromatic Alcohol $R^3$ is aryl as defined above. When trypsin hydrolyzes the substrate, trypsin cleaves the O—C single bond in the ester moiety of the compound of formula (I). This causes the formation of the compound $R^3$—OH. $R^3$ must be stable so that it does not form the compound $R^3$—OH absent the compound for formula (I) being cleaved by trypsin.

In one embodiment, $R^3$—OH is optically distinguishable from the compound of formula (I). In another embodiment, $R^3$—OH reacts with a diazonium salt to form a visible color, preferably, a color that is different from the color of the biological sample.

Generally $R^3$ can be any aryl compound such that the compound $R^3$—OH, when formed by trypsin cleaving the compound of formula (I), can be optically distinguished from the compound of formula (I) or reacts with a diazonium salt to form a color in the visible region. Preferably, $R^3$ comprises a heterocyclic aromatic moiety. Preferably, the heterocycle is in a fused ring system and the heteroatom is selected from the group consisting of N or O. Preferred $R^3$ groups may include, but are not limited to, phenylpyrrole and derivatives thereof, coumarin and derivatives thereof, phenylthlophene and derivatives thereof, indole and derivatives thereof, and 2-phenyl-5H-thiazol and derivatives thereof.

Diazonium Salts

A diazonium salt is generally an organic salt of a compound having a diazonium radical, a illustrated by the general structure:

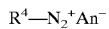

Wherein $R^4$ is an aryl moiety as defined previously and $^{An-}$ is an anion. An represents any suitable anion such as halide (for example chloride, bromide, fluoride and iodide), tetrafluoroborate, chlorozincate, hemizinc chloride, nitrate, perchlorate, $\rho$-toluenesulfonate and others readily apparent to one skilled in the art.

Other contemplated diazonium salts incorporate the anion in $R^4$ and are zwitterions having the structure:

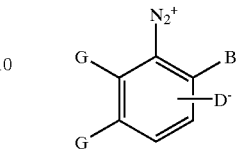

wherein $D^-$ is an anion. Preferred anions include $SO_3^-$, $CO_2^-$, and $PO_3^=$. G is independently H, $C_{1-6}$ alkyl, or in which the two G moieties together form a fused ring system. B is H or OH.

Any diazonium salt that reacts with the aromatic alcohol ($R^3$—OH) to form a color in the visible region may be used with the trypsin substrate. Preferred diazonium salts are those that do not readily react with other urinary components during the detection of UTI. A non-limiting list includes 2,4-dimethoxybenzene-diazonium tetrafluoroborate, 4-methoxynaphthalene-1-diazonium tetrafluoroborate, 2,5-dimethoxy-4-dimethylaminobenzene-diazonium tetrafluoroborate, 4-dimethylaminobenzenediazonium tetafluoroborate, 2-methoxy-4-(N-pyrrolidino)-benzenediazonium tetrafluoroborate, 2-methoxy-4-(N-piperidino)-benzene-diazonium tetrafluoroborate, 2,6-dimethoxy-4-(N-morpholino)-benzenediazonium tetrafluoroborate, 4-methoxy-2-(N-morpholino)-benzenediazonium hemizinc chloride (MMBD), 2-methoxy-4-[N-(N'-methyl)piperazino]-benzenediazonium tetrafluoroborate, 2-methoxy-4-(N-thiomorpholino)-benzendiazonium tetrafluoroborate and the like.

Preferred zwitterionic diazonium salts include 1-diazonphthalene-4-sulfonate, 1-diazo-2-naphthol-4-sulfonate, 1-diazo-2-naphthol-4,6-disulfonate, 1-diazophenyl-3-carbonate as disclosed in U.S. Pat. No. 4,637,979 (Skjold, et al.) which is hereby incorporated by reference.

Many diazonium salts useful herein are available from a number of commercial sources, and those not readily available can be prepared by a skilled organic chemist using available reagents and well-known procedures.

EXAMPLES

The following examples are provided to further assist the reader in making and using the present invention. Thus, preferred embodiments are described in experimental detail and analyzed as to the results. The examples are meant to be illustrative only, and are in no way intended to limit the scope of the invention described and claimed herein.

In this section, abbreviations are used as indicated:

$cm^{-1}$=reciprocal centimenters (wavenumbers)

g=gram kg=kilogram l=liter mL=milliliter

M=molar mM=millimolar

N=normal eq=equivalents mol=gram molecular formula (moles)

mmol=gram molecular formula X $10^{-3}$ (millimoles)

nm=nanometers aq=aqueous h=hour min=minutes tlc=thin layer chromatography mp=melting point dec=decomposition Infrared (IR) spectra were obtained with an ATI-Mattson RS-1 fourier transform infrared (FTIR) spectrometer in KBr unless otherwise noted; the 1602 $cm^{-1}$ band of polystyrene film was used as an external calibration standard. Signals are reported as $cm^{-1}$.

Fluorescence spectra were obtained using a Perkin-Elmer Model LS-5 Fluorescence Spectrophotometer. Excitation and emission wavelengths are reported in nanometers (nm).

Proton magnetic resonance ($^1$H NMR) spectra were obtained at 300.12 MHz using a General Electric GN 300 NB spectrometer; spectra were obtained in deuterated dimethylsulfoxide (DMSO-$d_6$) solution unless otherwise noted. Chemical shifts are reported in parts per million downfield from the internal standard tetramethylsilane.

Carbon-13 magnetic resonance ($^{13}$C NMR) spectra were obtained at 75.4 MHz using a General Electric GN 300 NB spectrometer with Fourier transform and with full proton broad-band noise decoupling; spectra were obtained in deuterated dimethylsulfoxide (DMSO-$d_6$) solution unless otherwise noted. Chemical shifts are reported in parts per million downfield from the internal standard tetramethylsilane.

Organic reagents and anhydrous solvents were obtained from Sigma-Aldrich Corporation and were used without purification, unless otherwise noted. Other solvents were HPLC grade from Malinckrodt Baker Incorporated unless otherwise noted. Inorganic reagents were ACS reagent grade from Fisher Scientific Company or other major vendor. Brine refers to a saturated aqueous sodium chloride solution.

Thin layer chromatography (tlc) was performed using silica gel 60F-254 plates from E. Merck. Column chromatography was performed using E. Merck Silica Gel 60 (70–230 mesh) or equivalent, unless otherwise noted. All melting points and boiling points are uncorrected.

The following experiments were performed to illustrate the synthesis of the ester of the present invention. While these experiments relate to specific starting materials and end products, it is believed that the procedures are applicable to a broad range of species contained within the generic class of esters disclosed herein.

Preparing the Trypsin Substrate

Generally, the trypsin substrate of the present invention is prepared by reacting the compound $R^3$—OH with a derivative of arginine that is protected at both the Nα and the $N_G$ and has had the OH group of the carboxylic acid moiety activated with a suitable leaving group, such as a halo atom. During the reaction, the O from $R^3$—OH replaces the leaving group, giving a compound of the formula (I).

Example 1

Synthesis of 3-(Nα-tosyl-$N_G$-nitro-L-argininyloxy)-5-phenylpyrrole (C)

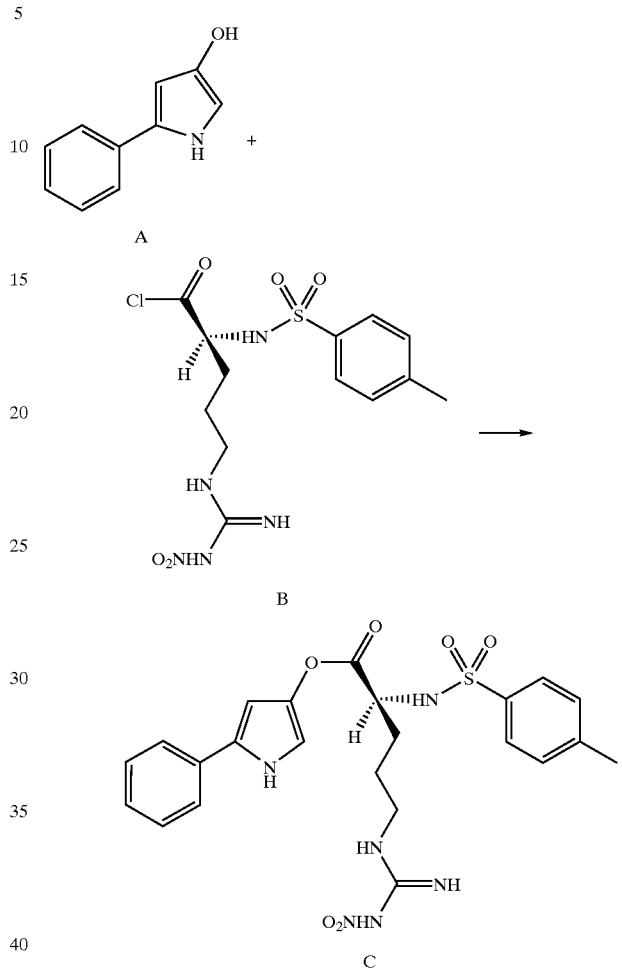

A dry 100 mL recovery flask maintained under an inert gas atmosphere was charged with anhydrous tetrahydrofuran (THF, 11.5 mL) then cooled in an ice bath. To this was added anhydrous pyridine (0.84 mL, 10.38 mmole) followed by trifluoroacetic acid (1.59 mL, 20.6 mmole). 3-hydroxy-5-phenylpyrrole (A) (Corey, et al. U.S. Pat. No. 4,657,855) (1.39 g, 8.73 mmole) was added at once to give a pink heterogeneous reaction mixture. A solution of B Nα-tosyl-$N_G$-nitro-L-argininyl chloride (Inouye, et al., Bull. Chem Soc. Japan 47(1), 202 (1974)) (4.08 g, 10.41 mmole) in anhydrous THF (15 mL) was placed in an addition funnel atop the reaction flask and added dropwise over about 5 min.

Upon completion of the addition, the funnel was rinsed with anhydrous THF (2 mL) and this was added to the reaction. The dark resulting solution was stirred at 0° C. for about 1½ hours then transfered using a minimum of THF to a separatory funnel containing 0.5 M citric acid (130 mL) and ethyl acetate (EtOAc, 130 mL). The funnel was shaken vigorously to separate the phases.

The citrate solution was backwashed with EtOAc (ca. 20 mL), then the the combined organic layer was washed with brine. The organic layer was extracted with saturated aq $NaHCO_3$ (100 mL). The aqueous extract was at once backwashed with ethyl acetate (EtOAc, 20 mL). The combined organic layers were washed with brine. The separated organic layer was for about 30 min over a mixture of MgSO$_4$ (23.4 g) and Darco® G-60 (American Norit Co., Inc.).

The organic layer was filtered with suction through Celite® 521 (Johns-Manville Corp.) and evaporated to dryness in vacuo to give a brownish foam. The foam was taken up in hot 100% ethanol (200 proof, EtOH) (22 mL) and allowed to cool. Once crystalline product began to separate, it was chilled on ice and refrigerated overnight. The product C was collected by filtration, washed with ice-cold 100% EtOH and vacuum dried to give the title compound as a light pink solid (3.07 g, 68%). The product C was recrystallized from boiling 2-butanone and vacuum dried at 100° C. for about 10 hours to afford the analytical sample.

IR (KBr) cm$^{-1}$ 3399, 3364, 3317, 1748, 1625, 1588, 1510, 1432, 1280, 1261, 1160, 1089, 765, 578.

$^1$H NMR (DMSO-d$_6$) σ 11.18 (br. s, 1H), 8.42 (d, J=8.8 Hz, 1H), 7.69 (d, J=8.2 Hz, 2H), 7.56 (d of d, J$_1$=7.7 Hz & J$_2$=0.9 Hz, 2H), 7.32–7.40 (m, 4H), 7.18 (t, J=7.3 Hz, 1H), 6.58 (m, 1H), 6.11 (m, 1H), 3.93–4.03 (m, 1H), 3.11 (br. q, J=6.3 Hz, 2H), 2.36 (s, 3H), 1.4–1.8 (m, 4H).

$^{13}$C NMR (DMSO-d$_6$) ppm 20.96, 24.57, 29.24, 55.36, 97.94, 97.94, 98.11, 108.16, 108.37, 123.34, 126.02, 126.48, 126.60, 128.48, 128.74, 129.52, 129.65, 132.33, 137.27, 138.17, 142.72, 159.33, 169.35.

| Anal. Calcd. for C$_{23}$H$_{26}$N$_6$O$_6$S: | | | |
|---|---|---|---|
| Theory: | C: 53.68 | H: 5.09 | N: 16.33 |
| Found: | C: 53.71 | H: 5.26 | N: 16.20 |

Example 2

Synthesis of 3-(Nα-tosyl-N$_G$-nitro-L-argininyloxy) indole

A. Synthesis of 3-hydroxyindole (indoxyl):

Indoxyl 1,3-diacetate (Sigma Chemical Co., St. Louis, Mo.) (10.0 g; 46.05 mmole) was suspended with stirring in thoroughly deoxygenated H$_2$O (200 mL), maintained under an inert gas atmosphere. NaOH (16 g) was added at once and the reaction mixture was heated at ca. 85° C. for 15 min. The reaction was cooled in an ice/salt bath to <5° C., then dropwise treated with a thoroughly deoxygenated solution of citric acid monohydrate (30.63 g) in H$_2$O (30 mL) at a rate that kept the reaction temperature <5° C. NaCl (30 g) was then added and the reaction stirred in the cold for 1 h. The greenish yellow solid product was collected by filtration with suction, washed with a minimum amount of deoxygenated, ice-cold aq 0.5 N citric acid and dried in vacuo overnight to give 3-hydroxyindole (4.94 g; 80%). This product was used without further purification.

B. Synthesis of 3-(Nα-tosyl-N$_G$-nitro-L-argininyloxy) indole:

A dry 25 mL flask maintained under an inert gas atmosphere was charged with anhydrous THF (5.0 mL) and anhydrous pyridine (2.3 mL), then cooled in an ice/salt bath with stirring. To this was added trifluoroacetic acid (0.415 mL) followed by indoxyl (0.514 g; 3.86 mmole). A solution of Nα-p-toluenesulfonyl-N$_G$-nitro-L-argininyl chloride (Inouye, et al., Bull. Chem Soc. Japan 47(1), 202 (1974)) (2.0 g; 5.1 mmole) in anhydrous THF (6.0 mL) was dropwise added over 6 min, and the reaction was allowed to stir in the ice/salt bath for 0.5 h.

The cooling bath was replaced with an ice water bath and stirring continued for 0.75 h, followed by stirring at ambient temperature for 0.5 h. The reaction mixture was blended into a mixture of aq 0.5 M citric acid (100 mL) and EtOAc (50 mL) and the phases separated. The aqueous layer was washed with EtOAc (3×25 mL) then the combined organic layers were washed sequentially with brine (25 mL), saturated aq NaHCO$_3$ (25 mL) and again with brine (25 mL). The organic layer was dried over MgSO$_4$ and Darco® G-60, filtered with suction through Celite® 521 and evaporated to dryness in vacuo to yield a light green foam (1.4 g).

This was chromatographed on silica gel (60 Å, 200–400 mesh) using methanol/chloroform (MeOH/CHCl$_3$; 9:91, v:v) solvent. The major product band [tlc R$_f$=0.26 MeOH/ CHCl$_3$ (9:91, v:v)] was collected and freed of solvent in vacuo to give 3-(Nα-tosyl-N$_G$-nitro-L-argininyloxy)indole (0.88 g, 47%) as a pale green foam. The product was obtained in crystalline form following crystallization from 2-butanone/i-propanol (1:10). Mp=188–191° C. (dec).

IR (KBr) cm$^{-1}$ 3473, 3395, 3326, 1756, 1628, 1611, 1457, 1393, 1341, 1280, 1219, 1163, 1127, 1090, 1073, 748, 665, 580, 549;

$^1$H NMR (DMSO-d$_6$) σ 10.97 (s, 1H), 8.51 (d, J=8.5 Hz, 1H), 7.72 (d, J=8.2 Hz, 2H), 7.34 (d, J=8.3 Hz, 2H), 7.07–7.20 (m, 3H), 6.98 (t, J=7.2 Hz, 1H), 4.05–4.15 (m, 1H), 3.34 (br s, 4H) (HOD+exchangeable N—H), 3.14 (q, J=6.3 Hz, 2H), 2.35 (s, 3H), 1.4–1.9 (m, 4H);

$^{13}$C NMR (DMSO-d$_6$) ppm 20.8, 24.7, 29.3, 55.3, 111.7, 114.2, 116.9, 118.8, 119.2, 121.7, 126.4, 128.5, 129.5, 133.1, 138.1, 142.7, 159.3, 169.5 (3 coincident resonances).

Example 3

Synthesis of 4-(Nα-tosyl-N$_G$-nitro-L-argininyloxy)-2-phenyl-5H-thiazole

A solution of 2-phenyl-4(5H)-thiazolone (Jensen and Crossland, Acta Chem. Scand. 17, 144 (1963)) (0.738 g; 4.16 mmole) and 4-(dimethylamino)pyridine (0.615 g; 5.03 mmole) in anhydrous THF (8.0 mL) was cooled to 0° C. and maintained under an inert gas atmosphere. This was dropwise treated over 12 min with a solution of Nα-p-toluenesulfonyl-N$_G$-nitro-L-argininyl chloride (1.96 g; 5 mmole; 1.2 eq) in anhydrous THF (14 mL). After stirring for 2 hours the reaction was thoroughly blended into a mixture of EtOAc (100 mL) and 0.5M aq. citric acid (100 mL), and the phases separated.

The organic layer was washed sequentially with 25 mL portions of brine, saturated aq. NaHCO$_3$ and brine, then dried over MgSO$_4$ and Darco® G-60, filtered and evaporated to dryness in vacuo to give a yellow foam (1.9 g). This was chromatographed on silica gel (60 Å, 200–400 mesh, 190 g) using acetone/hexane (1:1, v:v) solvent. Fractions containing the major product (Rf=0.22) were combined and evaporated to dryness in vacuo to give a pale yellow foam (1.05 g). This crude product was taken up in warm CHCl$_3$ (7 mL) and spontaneously crystallized. The product was collected by filtration, washed with cold CHCl$_3$ and dried under reduced pressure to give the title compound (0.77 g) as tiny pale yellow needles with mp=134–5° C. (dec).

IR(KBr) cm$^{-1}$ 3410, 3309, 3165, 17671635, 1599, 1517, 1497, 1431, 1327, 1291, 1160, 1010, 763, 659, 585;

$^{13}$C NMR (DMSO-d$_6$) ppm 20.99, 24.54, 28.93, 39.85, 55.33, 104.94, 125.62, 126.51, 129.38, 129.63, 130.78, 132.36, 138.02, 142.87, 153.30, 159.33, 164.19, 169.14 (4 coincident resonances).

Example 4

Synthesis of 3-(Nα-tosyl-$N_G$-tosyl-L-argininyloxy)-5-phenylpyrrole

A. Synthesis of Nα-tosyl-$N_G$-tosyl-L-arginine:

A 500 mL, one neck, round-bottom flask was charged with 2N aq. NaOH (130 mL, 260 mmole). Sodium carbonate (4.2 g, 39.66 mmole), was added in small portions. After the solid dissolved (10 min), $N_G$-tosyl-L-arginine (Advanced ChemTech, Louisville, Ky.) (13 g, 39.66 mmole) was added. The mixture was stirred until the solid dissolved (15 min) and became a clear yellow solution. A solution of p-toluenesulfonyl chloride (11.33 g, 59.45 mmole) in acetone (50 mL) was added dropwise from an addition funnel to the reaction solution stirred in an ice/water bath.

After the addition (15 min), the resulting mixture was stirred in an ice/water bath for 3 h. The initial white solid slowly dissolved to give a fine suspension after 3 h. The reaction mixture was filtered with suction through a Celite® 521 pad. The pad was washed with water (2×20 mL) and the resulting filtrate was concentrated under vacuum to remove the acetone. The resulting light yellow cloudy residue was stirred and cooled in an ice/water bath. Then 6N aq. HCl was added dropwise until pH 2. To the resulting white gummy precipitate was added ethyl acetate (100 mL).

The mixture was shaken in the flask and the resulting emulsion was filtered with suction through a Celite® 521 pad. The layers were separated and the aqueous layer was extracted with ethyl acetate (3×100 mL). The combined organic layers were washed with 0.1N aq. HCl (2×100 mL) and saturated aq. NaCl (100 mL). The solution was then stirred over magnesium sulfate (25 g) for 30 min. The mixture was filtered with suction and the filtrate was concentrated under vacuum to give a yellow viscous oil. The oil was dried overnight under vacuum to give an amorphous yellow solid (4.6 g, 24%). This product was used without further purification.

IR (KBr) cm$^{-1}$ 3440, 3348, 3260, 3065, 2929, 1721, 1629, 1596, 1548, 1401, 1329, 1084, 815, 674, 565

$^1$H NMR (DMSO-$d_6$) σ 8.0 (d, J=9 Hz, 1H), 7.65 (d, J=7 Hz, 2H), 7.62 (d, J=7 Hz, 2H), 7.34 (d, J=8 Hz, 2H), 7.27 (d, J=8 Hz, 2H), 3.61 (m,1H), 2.96 (br q, J=6.3 Hz, 2H), 2.38 (s, 3H), 2.35 (s, 3H), 1.3–1.6 (m, 4H)

$^{13}$C NMR (DMSO-$d_6$) ppm 20.85, 20.94, 29.39, 55.29, 125.49, 126.45, 129.00, 129.34, 142.43, 172.52.

B. Synthesis of 3-(Nα-tosyl-$N_G$-tosyl-L-argininyl chloride:

A dry 250 mL one-neck, round-bottom flask was charged with anhydrous THF (18 mL). After Nα-tosyl-$N_G$-tosyl-L-arginine (1.5 g, 3.1 mmole) was added to the solvent, the solution was cooled in an ice/water bath. Phosphorous pentachloride (PCl$_5$, 1.14 g, 5.6 mmole) was added in small portions and the resulting mixture was stirred until the solid dissolved (30 min). The solution was warmed to RT and stirred 30 min. Additional PCl$_5$ (0.5 g) was added and the mixture stirred for another 1 h. The solution was cooled in an ice/water bath and hexane (90 mL) was added. A white mass came out of solution. The solution sat in an ice/water bath for 15 min then the mixture was cooled in acetone/dry ice bath for 15 min. The hexane was decanted off and the residue was washed with hexane (2×10 mL). The resulting mass was dried overnight under vacuum and became a white amorphous solid (1.31 g, 84%). The product was used without further purification.

C. Synthesis of 3-(Nα-tosyl-$N_G$-tosyl-L-argininyloxy)-5-phenylpyrrole:

A dry 25-mL one-neck, round-bottom flask maintained under an inert gas atmosphere was charged with anhydrous THF (3 mL) and triflouroacetic acid (0.41 mL). After the solution had been cooled in an ice/water bath, anhydrous pyridine (0.22 mL) was added dropwise. The solution was stirred 10 min then 3-hydroxy-5-phenylpyrrole (332 mg, 2.09 mmole) was added in small portions. The solution became a maroon mixture that was stirred 10 min.

Then, a solution of 3-(Nα-tosyl-$N_G$-tosyl-L-argininyl chloride (1.31 g, 2.61 mmole) in anhydrous THF (3 mL) was added dropwise via syringe. The syringe was washed with THF (2×0.5 mL) and the washes were added to the reaction. The resulting dark reaction was stirred 2 h in an ice/water bath. Then the reaction was blended into EtOAc (30 mL) and 1M aq. citric acid (30 mL). The layers were mixed and separated. The organic layer was washed again with 1M citric acid (20 mL). The combined citric acid layer was extracted with ethyl acetate (20 mL). The combined organic layer was washed with saturated aq. sodium bicarbonate (2×20 mL). The combined sodium bicarbonate layer was extracted with ethyl acetate (2×20 mL). The combined ethyl acetate layer was extracted with sat aq. sodium chloride (2×20 mL).

Then, the solution was stirred over magnesium sulfate (5 g) and Norit® A (American Norit Co., Inc.) (1 g) for 30 min. The mixture was filtered with suction through Celite® 545. The filtrate was treated again with Norit® A and filtered with suction through Celite® 545, then concentrated under reduced pressure to give a brown viscous oil (1.01 g). The brown viscous oil was purified by silica gel chromatography (40 g; solvent: ethyl acetate: hexane, 2.5:1, v:v). The fractions containing product (Rf=0.3) were collected and concentrated under reduced pressure to afford tan viscous oil. The oil was dried overnight under vacuum to give the title product as a tan amorphous solid (0.56 g, 43%).

IR (KBr) cm$^{-1}$ 3439, 3345, 1750, 1623, 1574, 1549, 1511, 1455, 1402, 1327, 1306, 1257, 1207, 1160, 1131, 1082, 815, 763, 693, 672, 572, 554

$^{13}$C NMR (DMSO-d6) ppm 14.1, 2096, 24.58, 29.24, 29.35, 55.36, 59.75, 98.02, 108.25, 125.34, 126.53, 126.73, 128.48, 128.73, 129.57, 132.32, 137.27, 138.17, 142.7, 159.33, 169.33, 170.3.

Example 5

Synthesis of 7-(Nα-tosyl-$N_G$-nitro-L-argininyloxy)-4-methylcoumarin

7-Hydroxy-4-methylcoumarin (0.7047 g, 4 mmole) was dissolved with warming in a mixture of anhydrous THF (10.0 mL) and anhydrous pyridine (0.65 mL), maintained under an inert gas atmosphere. The stirred solution was cooled to −66 to −68° C. then treated dropwise, over about 6 min, with a solution of Nα-p-toluenesulfonyl-$N_G$-nitro-L-argininyl chloride (2.00 g, 5.1 mmole) in anhydrous THF (13 mL). The mixture was maintained below −57° C. for about 45 min, then warmed to 0° C. and stirred for an additional 45 min. The reaction mixture was transferred to a separatory funnel containing EtOAc (80 mL) and 0.5M aq. citric acid (50 mL), using a minimum amount of MeOH to mobilize the tarry product that separated. The mixture was vigorously shaken and the phases were allowed to separate.

The organic layer was extracted with another portion of 0.5M citric acid (50 mL), then the combined citrate layers were washed with EtOAc (50 mL). The combined organic layers were washed sequentially with brine (30 mL), saturated aq. NaHCO$_3$ (2×40 mL) and brine (40 mL), then dried over a mixture of MgSO4 and Darco® G-60. The mixture was filtered through Celite® 521 and evaporated to dryness in vacuo to yield a light yellow foam (1.88 g). This foam was chromotographed on silica gel (190 g) using acetone/EtOAc (4:96, v:v) solvent. Fractions containing the major product band (Rf=0.25) were combined and concentrated in vacuo from a 30° C. bath. Toward the end of this concentration (ca. 35 mL remaining) the product began to separate as a mixture of oil and solid. The concentration was halted and the mixture stirred, first at ambient temperature then at 0° C. as the oil became solid. After about an hour the solid was filtered, washed with cold EtOAc then hexane and vacuum dried to give the title compound (0.72 g) as a fine white powder.

IR (KBr) cm$^{-1}$ 3418, 1765, 1730, 1708, 1626, 1613, 1420, 1390, 1338, 1264, 1158, 1131, 1091, 666, 576, 551.

$^1$H NMR (DMSO-d$_6$). sigma. (Recorded at 400.13 MHz) 8.59 (d, J=8.6 Hz, 1H [N—H]), 8.54 (v br s, 1H [N—H]), 7.80 (d, J=8.8 Hz, 1H), 7.73 (d, J=8.3 Hz, 2H), 7.40 (d, J=8.4 Hz, 2H), 6.88 (d of d, J$_1$=8.7 Hz and J$_2$=2.3 Hz, 1H), 6.74 (s, 1H), 6.42 (d, J=1.2 Hz, 1H), 4.05–4.15 (in, 1H), 3.36 (s, 2H)(HOD+exchangeable N—H), 3.11–3.19 (m, 2H), 2.43 (s, 3H), 2.39 (s, 3H), 1.45–1.90 (m, 4H).

The Diagnostic Device

Another aspect of the present invention involves a diagnostic device comprising a carrier maxtrix and a compound of the formula (I).

The nature of the material of such carrier matrix can be of any substance capable of used with the trypsin substrate of the present invention and the diazonium salt of the present invention. Preferably, the carrier matrix comprises a bibulous material, such as filter paper. Other preferred materials may include those disclosed in U.S. Pat. No. 3,846,247, which describes felt, porous ceramic strips, and woven or matted glass fibers. As substitutes for paper, U.S. Pat. No. 3,552,928 describes the use of wood sticks, cloth, sponge material, and argillaceous substances.

The use of synthetic resin fleeces and glass fiber felts in place of paper is suggested in British Patent No. 1,369,139, and British Patent No. 1,349,623 teaches the use of a light-permeable meshwork of thin filaments as a cover for an underlying paper matrix. These references also teach impregnating the paper with part of a reagent system and impregnating the meshwork with other potentially incompatible reagents. French Patent No. 2,170,397 describes the use of carrier matrices having greater than 50% polyamide fibers therein.

Another approach to carrier matrices is described in U.S. Pat. No. 4,046,513 wherein the concept of printing reagents onto a suitable carrier matrix is employed. U.S. Pat. No. 4,046,514 describes the interweaving or knitting of filaments bearing reagents in a reactant system. All such carrier matrix concepts can be employed in the present invention, as can others. The carrier matrix can also comprise a system that physically entraps the assay reagents, such as polymeric microcapsules, which then rupture upon contact with the test sample. It can comprise a system wherein the assay reagents are homogeneously combined with the carrier matrix in a fluid or semi-fluid state, which later hardens or sets, thereby entrapping the assay reagents.

There are many possible ways to prepare such a diagnostic device. One preferred way is to contact the carrier matrix with a buffer solution, dry the carrier matrix, and then contact the carrier matrix with a solution comprising the trypsin substrate of formula (I). Preferably, the carrier matrix is then dried. The solution comprising the trypsin substrate preferably also comprises a diazonium salt.

One diagnostic device is a diagnostic kit for determining the presence of urinary trypsin inhibitor in a biological fluid comprises trypsin and a trypsin substrate of the formula (I). In one preferred embodiment, the diagnostic kit also comprises a reagent capable of being used to determine the presence of urinary trypsin inhibitor such that the greater the intensity of the color, the less urinary trypsin inhibitor is in the biological sample. In this embodiment, the reagent is preferably a diazonium salt. In another preferred embodiment R$^3$—OH is a different color from the biological sample such that the two colors are distinguishable with the naked eye. In this embodiment, the greater the intensity of the color, the less urinary trypsin inhibitor is in the biological sample.

Testing for the Presence of UTI

A preferred method of detecting levels of urinary trypsin inhibitor in a biological sample (preferably a urine sample) comprises contacting the biological sample with a predetermined amount of trypsin, a predetermined amount of a diazonium salt, and a trypsin substrate of the formula (I). The trypsin substrate can optionally be on or in a diagnostic device as defined above. One advantage of this embodiment is that no blood sample is required. Urine samples are preferred because they can be collected easily (especially in pediatric care) and require no pretreatment.

Trypsin cleaves the ester bond in the trypsin substrate of the formula (I). Then R$^3$—OH is liberated. In one embodiment, R$^3$—OH is itself optically distinguishable from the compound of formula (I) (either with the naked eye or with analytical instrumentation). In another embodiment, R$^3$—OH reacts with a diazonium salt to form a visible color. The greater the intensity of the color, the less UTI is in the biological sample.

Example 6 demonstrates the effectiveness of the trypsin substrate of formula (I) for detecting the effectiveness of the trypsin substrate of formula (I) for detecting levels of UTI in a biological sample.

Example 6

Dry-phase Analytical Element for UTI Measurement

Reagent strips were made according to the following procedure: Filter paper (240 C grade from Ahlstrom Inc.) was saturated with the first dip solution and dried for 2 minutes at 80° C. and 4 minutes at 60° C. The resultant paper was then saturated with the second dip solution and dried for 6 minutes at 50° C. to form the completed reagent paper. Adhesive (Y9494 from 3M Inc.) was applied to the reagent paper and it was affixed to a polystyrene handle in the form of pads, which were 0.20 inch×0.20 inches square.

A. Composition of the First Dip:
  a. Water
  b. Bicine Buffer (600 mM)
  c. Ethylene glycol bis (β-aminoethyl ether) N,N,N',N'-tetra-acetic acid (EGTA) (5.1 mM)
  d. Plasdone (PVP K30 from Sigma-Aldrich) (1.75% by weight)
  e. MgSO$_4$ (660 mM)
  f. Bovine Pancreatic Trypsin (Calbiochem Cat. No. 6502) (272 units/mL)
  g. Adjust to pH 8.00±0.02 with 1N NaOH.

B. Composition of the Second Dip:
  a. Acetone
  b. Trypsin substrate (Example 1, 2 or 4 product) (1.25 mM)
  c. 2-Methoxy-4-morpholinobenzene diazonium chloride, zinc chloride double salt (MMBD) (diazonium coupling agent) (2.0 mM)
  d. KOK-10071 polymer (from Bayer Corporation) (0.1% by weight)

Data were obtained by dipping the strips into the samples set out in Table 1 and placing them in a Clinitek™ 50 spectrometer from Bayer Diagnostics to collect data at 15 and 60 seconds after dipping. Decode values were calculated using the equation:

$$\text{decode} = \{[(B_{15}+G_{15})-(B_{60}+G_{60})]/(B_{15}+G_{15})\} * 1000$$

Where:

$B_{15}$ is the reflectance of the blue wavelength at 15 seconds, $B_{60}$ is the reflectance of the blue wavelength at 60 seconds, $G_{15}$ is the reflectance of the green wavelength at 15 seconds, and $G_{60}$ is the reflectance of the green wavelength at 60 seconds.

The results of this experiment are presented in Table 1.

TABLE 1

| Trypsin Substrate | Negative Sample | Positive Sample |
| --- | --- | --- |
| Example 1 | 474 | 212 |
| Example 2 | 422 | 168 |
| Example 4 | 61 | 30 |

Negative Sample = Water
Positive Sample = Water with 200 IU/mL of urine trypsin inhibitor (ulinastatin; Miraclid ™, Mochida Pharmaceutical Co., Ltd. Yotsuya Tokyo Japan)
Example 1 = 3-(Nα-tosyl-N$_G$-nitro-L-argininyloxy)-5-phenylpyrrole
Example 2 = 3-(Nα-tosyl-N$_G$-nitro-L-argininyloxy)indole
Example 4 = 3-(Nα-tosyl-N$_G$-tosyl-L-argininyloxy)-5-phenylpyrrole Negative Sample=Water
Positive Sample=Water with 200 IU/mL of urine trypsin inhibitor (ulinastatin; Miraclid™, Mochida Pharmaceutical Co., Ltd. Yotsuya Tokyo Japan)
  Example 1=3-(Nα-tosyl-N$_G$-nitro-L-argininyloxy)-5-phenylpyrrole
  Example 2=3-(Nα-tosyl-N$_G$-nitro-L-argininyloxy)idole
  Example 4=3-(Nα-tosyl-N$_G$-tosyl-L-argininyloxy)-5-phenylpyrrole Each of these synthetic trypsin substrates was active with trypsin enzyme, allowing a change in decode signal of more than 50% when trypsin was substantially inhibited by the trypsin inhibitor.

Example 7

Dry-phase Analytical Element for Trypsin Detection Using the Example 3 Substrate Reagent strips were made according to the following procedure: Filter paper (240 C grade from Ahlstrom Inc.) was saturated with the first dip solution and dried at ambient temperature for 2 hours, then at 110° C. for 5 minutes. The resultant paper was saturated with the second dip solution and dried for about 1 minute at 60° C. to form the completed, white reagent paper. The paper was then cut into pads, which were 0.25 inch×0.25 inches square.

A. Composition of the First Dip:
  a. Water (25.0 mL)
  b. Ethylene glycol bis (β-aminoethyl ether) N,N,N',N'-tetra-acetic acid (EGTA) (0.06 g)
  c. Plasdone (PVP K30 from Sigma-Aldrich) (0.438 g)
  d. MgSO$_4$ (1.08 g)

B. Composition of the Second Dip:
  a. Acetone (7.75 mL)
  b. Example 3 trypsin substrate (4-(Nα-tosyl-N$_G$-nitro-L-argininyloxy)-2-phenyl-5H-thiazole, 3.1 mg)
  c. 2-Methoxy-4-morpholinobenzene diazonium chloride, zinc chloride double salt (MMBD) (diazonium coupling agent) (2.5 mg)

Identical pads were separately wetted with 25 μL portions of two different test solutions. One test solution was 50 mM pH=8 phosphate buffer (control solution) and the second was 50 mM pH=8 phosphate buffer containing 10,000 U/mL of bovine pancreatic trypsin (test solution). Within one minute the pad treated with the test solution had turned blue while the pad treated with the control solution remained white.

Example 8

Dry-phase Analytical Element for Trypsin Detection Using the Example 5 Substrate Reagent strips were made according to the following procedure: Filter paper (240 C grade from Ahlstrom Inc.) was saturated with the first dip solution and dried at ambient temperature for 2 hours, then at 110° C. for 5 minutes. The resultant paper was saturated with the second dip solution and dried for about 1 minute at 60° C. to form the completed, white reagent paper. The paper was then cut into pads, which were 0.25 inch×0.25 inches square.

A. Composition of the First Dip:
  a. Water (24.55 mL)
  b. Ethylene glycol bis (β-aminoethyl ether) N,N,N',N'-tetra-acetic acid (EGTA) (0.06 g)
  c. Plasdone (PVP K30 from Sigma-Aldrich) (0.876 g)
  d. MgSO$_4$ (1.08 g)

B. Composition of the Second Dip:
  a. Acetone (9.3 mL)
  b. Acetic acid (0.108 mL)
  c. Example 5 trypsin substrate (7-(Nα-tosyl-N$_G$-nitro-L-argininyloxy)-4-methylcoumarin, 5.0 mg)

Identical pads were separately wetted with 25 μL portions of two different test solutions and viewed under long wavelength (365 nm) ultraviolet light illumination. One test solution was 50 mM pH=7 phosphate buffer (control solution) and the second was 50 mM pH=7 phosphate buffer containing 10,000 U/mL of bovine pancreatic trypsin (test solution). Within one minute the pad treated with the test solution was fluorescing brightly while the pad treated with the control solution remained dull and non-fluorescent.

Trypsin concentrations may be instrumentally determined with the reagent pads in a modified liquid assay. Three reagent pads are extracted with 2.0 mL of 50 mM pH=7 buffer containing 0–20 u/mL of trypsin. Fluorescent emission at 385 nm is measured with a Perkin-Elmer Model LS-5 fluorescence spectrophotometer using excitation at 335 nm, and is reported in luminescence units (LU). The rate of increase of emission at 385 nm was determined graphically from the plot of LU vs. time output by the instrument. Rates were obtained for 4 trypsin concentrations and are shown in Table 2.

TABLE 2

| Trypsin concentration (U/mL) | Rate of 385 nm emission increase (LU/mm) |
|---|---|
| 0 | 0.36 |
| 5 | 1.21 |
| 5 | 2.35 |
| 10 | 2.38 |
| 10 | 2.08 |
| 20 | 3.75 |
| 20 | 3.75 |

A linear regression analysis of the data in Table 2 returned the following equation:

$$U/mL = (LU/min - 0.451)/0.167$$

The rate at which the fluorescent emission at 385 nm increases is directly proportional to the amount of enzyme present.

Of course, it should be understood that a wide range of changes and modifications can be made to the embodiments of the present invention as described above. It is intended, therefore, that the foregoing description illustrates rather than limits this invention, and that it is the appended claims, including all equivalents, that define this invention.

What is claimed is:

1. A diagnostic device comprising:
   a carrier matrix; and
   a compound of the formula (I)

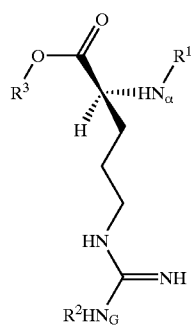

(I)

wherein $R^1$ is a protecting group for $N\alpha$;
   $R^2$ is a protecting group for $N_G$; and
   $R^3$ is aryl;
   wherein the compound of formula (I) is a trypsin substrate such that trypsin cleaves the O—C single bond, which liberates $R^3$—OH.

2. The diagnostic device of claim 1 wherein $R^1$ is selected from the group consisting of acyl, arene sulfonyl, and carbamoyl derivatives.

3. The diagnostic device of claim 1 wherein $R^1$ is selected from the group consisting of t-butyloxycarbonyl and derivatives, benzyloxycarbonyl and derivatives, benzoyl and derivatives, and benzene sulfonyl and derivatives.

4. The diagnostic device of claim 1 wherein $R^2$ is selected from the group consisting of nitro, arene sulfonyl, carbamoyl, and acyl.

5. The diagnostic device of claim 1 wherein $R^2$ is selected from the group consisting of nitro, benzene sulfonyl and derivatives, tosyl, carbobenzyloxy and derivatives, and benzoyl and derivatives.

6. The diagnostic device of claim 1 wherein $R^3$ comprises a heterocyclic aromatic moiety.

7. The diagnostic device of claim 6 wherein $R^3$ is a fused ring system.

8. The diagnostic device of claim 1 wherein $R^3$ is carbocyclic.

9. The diagnostic device of claim 8 wherein $R^3$ is 1-naphthol and derivatives thereof.

10. The diagnostic device of claim 1 wherein $R^3$ is selected from the group consisting of phenylpyrrole and derivatives thereof, coumarin and derivatives thereof, phenylthiophene and derivatives thereof, indole and derivatives thereof, and 2-phenyl-5H-thiazol and derivatives thereof.

11. The diagnostic device of claim 1 wherein the carrier matrix is filter paper.

12. The diagnostic device of claim 1 wherein the carrier matrix contains a diazonium salt.

13. The diagnostic device of claim 12 wherein $R^3$—OH reacts with a diazonium salt to form a visible color.

14. The diagnostic device of claim 12 wherein the diazonium salt has the structure:

$$R^4—N_2^+An^-$$

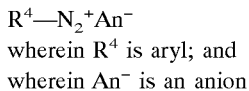

wherein $R^4$ is aryl; and
wherein $An^-$ is an anion.

15. The diagnostic device of claim 14 wherein $R^4$ is morpholinobenzene and derivatives thereof.

16. The diagnostic device of claim 12 wherein the diazonium salt is a zwitter ion having the structure

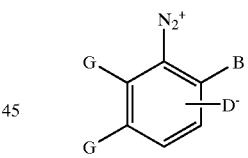

wherein $D^-$ is an anion;
wherein G is independently H, $C_{1-6}$ alkyl, or in which the two G moieties together form a fused ring system; and
wherein B is H or OH.

17. The diagnostic device of claim 1 wherein $R^3$—OH is optically distinct from the compound of formula (I).

* * * * *